United States Patent

Pokras

[11] Patent Number: 5,807,340
[45] Date of Patent: Sep. 15, 1998

[54] SELF REFILLING I.V. SYRINGE

[76] Inventor: Norman M. Pokras, 4448 Village Rd., Long Beach, Calif. 90808

[21] Appl. No.: 473,784

[22] Filed: Jun. 6, 1995

[51] Int. Cl.⁶ .................................................. A61M 5/178
[52] U.S. Cl. .......................... 604/183; 604/209; 604/234
[58] Field of Search ............................ 604/183, 208–210, 604/223, 224, 135, 131, 134, 61, 70, 72, 232, 181, 187, 188, 233, 234, 235, 236, 121, 218, 228, 246, 247; 433/81, 89, 90; 128/765; 606/115

[56] References Cited

U.S. PATENT DOCUMENTS

| | | |
|---|---|---|
| 1,170,805 | 2/1916 | Eastman . |
| 1,250,965 | 12/1917 | Capwell .................................. 604/223 |
| 1,282,000 | 10/1918 | Quayle . |
| 2,074,401 | 3/1937 | Kauzal ................................. 604/208 X |
| 2,316,095 | 4/1943 | Mead, Jr. ............................... 604/209 |
| 2,748,767 | 6/1956 | Wright . |
| 2,892,457 | 6/1959 | Sturtz .................................. 604/224 X |
| 3,517,668 | 6/1970 | Brickson ................................ 604/209 |
| 3,518,990 | 7/1970 | Banker .................................. 604/70 |
| 3,526,225 | 9/1970 | Isobe .................................. 604/183 X |
| 4,014,331 | 3/1977 | Head . |
| 4,333,457 | 6/1982 | Marguilies . |
| 4,382,789 | 5/1983 | Colombo et al. . |
| 4,472,141 | 9/1984 | Dragan . |
| 4,512,767 | 4/1985 | Denance ................................ 604/137 |
| 4,518,387 | 5/1985 | Murphy et al. . |
| 4,594,073 | 6/1986 | Stine . |
| 4,738,664 | 4/1988 | Prindle . |
| 4,861,339 | 8/1989 | Jonischkeit . |
| 4,968,303 | 11/1990 | Clarke et al. . |
| 5,033,961 | 7/1991 | Kandler et al. . |
| 5,115,816 | 5/1992 | Lee . |
| 5,228,883 | 7/1993 | Blakely et al. . |
| 5,288,285 | 2/1994 | Carter . |

Primary Examiner—Corrine M. McDermott
Assistant Examiner—A. T. Nguyen
Attorney, Agent, or Firm—Fulwider Patton Lee & Utecht, LLP

[57] ABSTRACT

A self refilling syringe for administering medicinal fluid to a patient including a removable syringe body having a plunger chamber formed at its front end with a connector port. A plunger is received in the chamber from an open end opposite the connector port and includes a plunger head on one end and a piston on the other end. The forward end of the syringe body includes a hub device mounted on the front end of the syringe body and is formed with a filler port and an applicator port in communication with the connector port. A filler check valve and an applicator check valve are disposed in the respective filler and applicator ports. Upon application of a positive pressure to the filler and applicator check valves from the chamber, the applicator check valve closes and the filler check valve opens to discharge fluid through the applicator port. Upon application of a partial vacuum to the filler and applicator check valves from the chamber, the filler check valve opens and the applicator check valve closes to draw a replenishing volume of fluid into the chamber through the filler port refilling the syringe chamber.

5 Claims, 2 Drawing Sheets

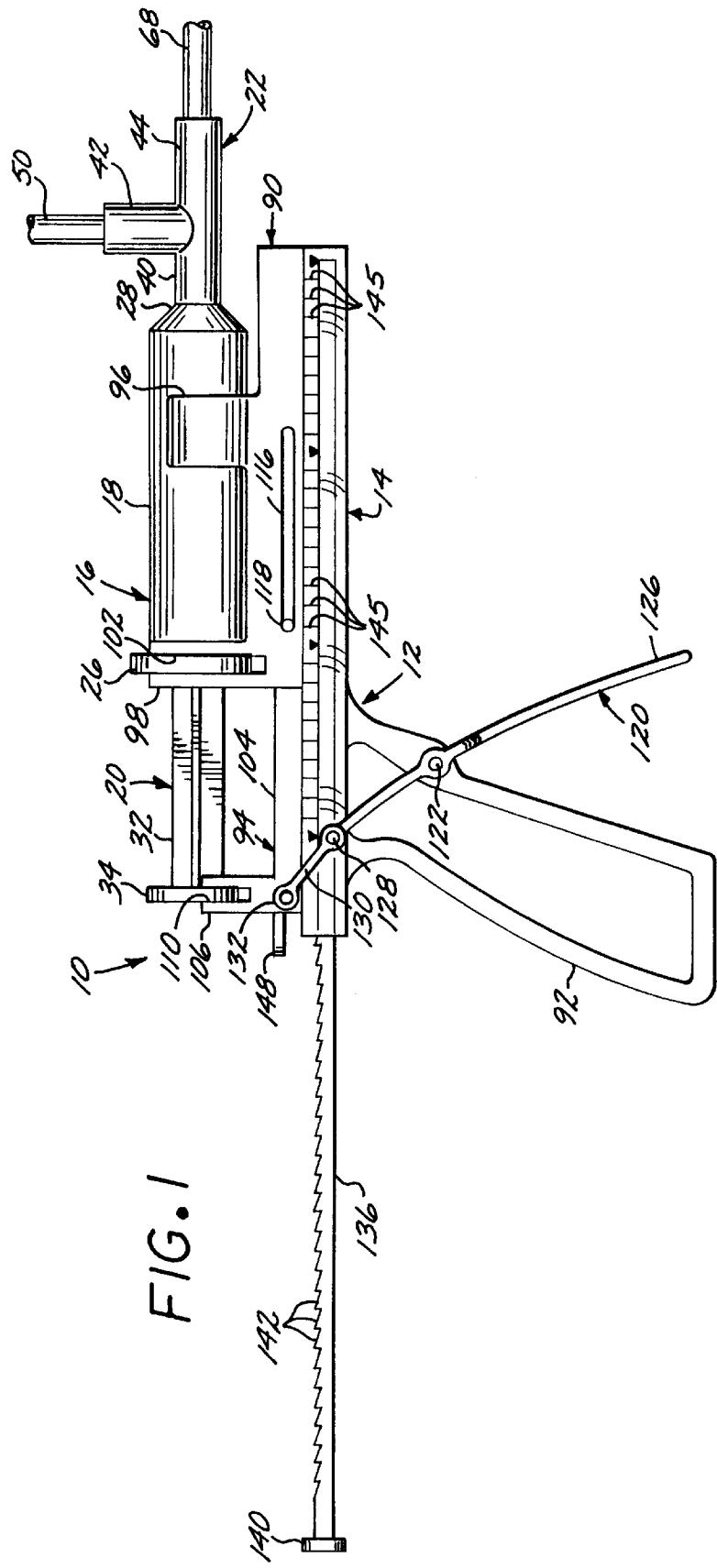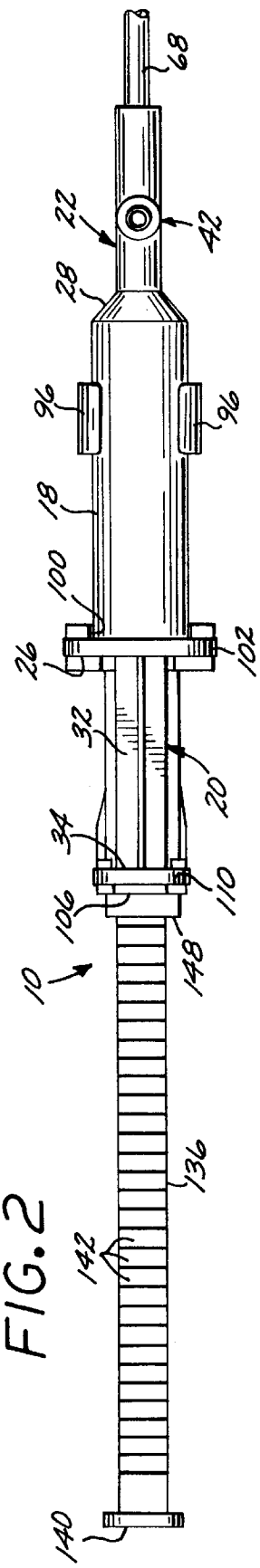

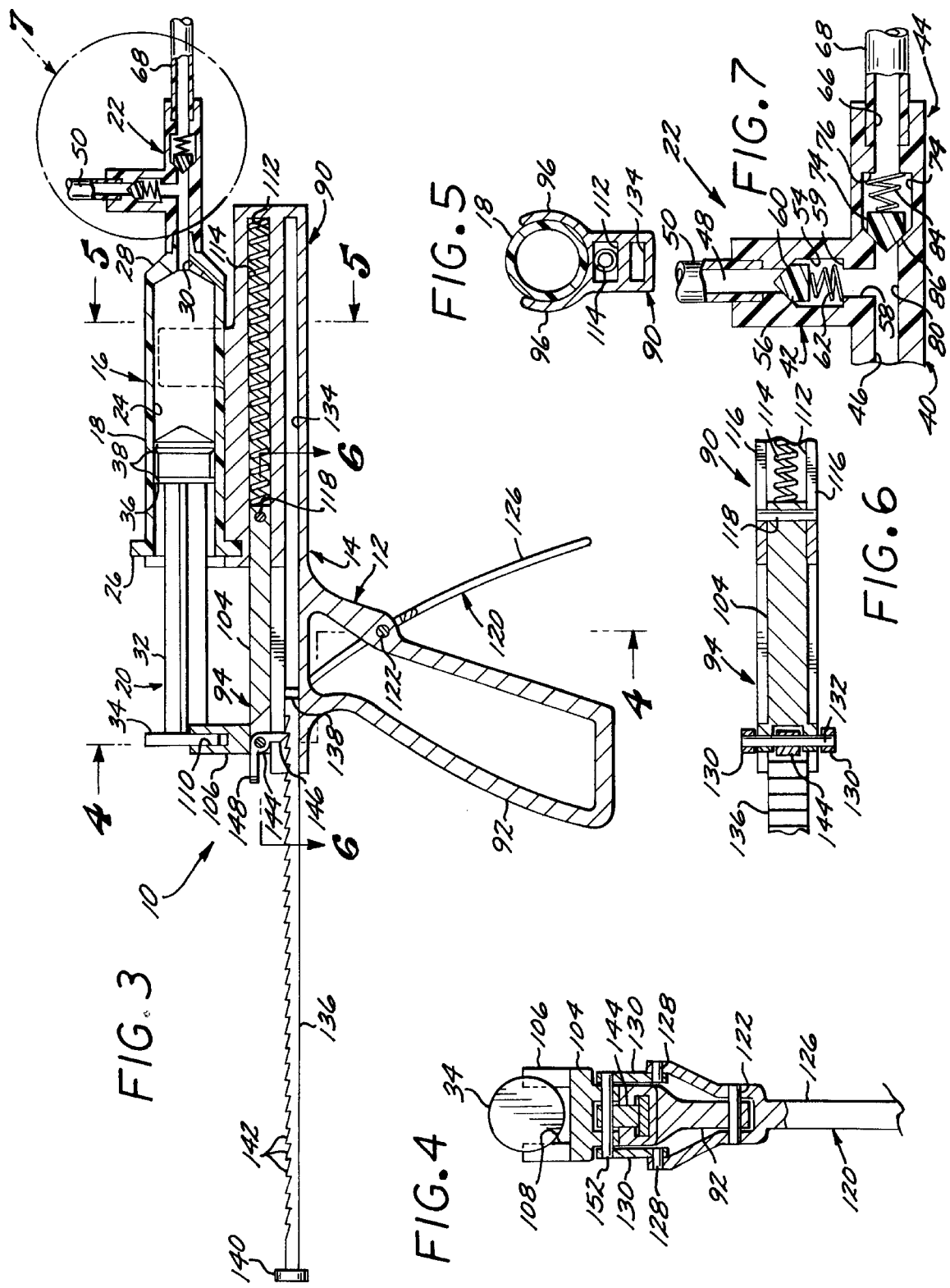

SELF REFILLING I.V. SYRINGE

BACKGROUND OF THE INVENTION

1. Field of the Invention

The present invention is related to devices for administering medicinal fluids to patients, and more particularly to syringes for dispensing such fluid.

2. Description of the Prior Art

It is well known that in order to minimize discomfort to a patient during invasive surgical medical and dental procedures, a general anesthetic solution may be intravenously administered to the patient inducing the patient into general anesthesia. In more complicated surgical procedures, the duration of the procedure may be lengthy making it necessary to administer a large continuous volume of general anesthetic to the patient or, in some instances, administer multiple injections of anesthetic.

In general, anesthetic solutions may be injected into the vascular system using a conventional syringe, typically having a relatively small volume capacity. In extended surgical procedures requiring the administration of multiple injections of anesthetic, the clinician must periodically interrupt the procedure at hand, retrieve a new sterile syringe, manually aspirate a volume of anesthetic from a fluid supply to fill the new syringe and then administer the next volume of anesthetic to the patient. In many such procedures, it may be necessary to exchange syringes a number of times over the duration of the procedure and during each such exchange, the clinician is, at least momentarily, distracted from the procedure then under way. In addition, the time required to make such syringe exchanges lengthens the duration of the procedure. Furthermore, the responsibility falls on the clinician to keep track of the number of times a syringe has been refilled and exchanged so that a cumulative total volume of anesthetic administered can be monitored, again tending to direct the clinicians attention periodically away from the matter at hand.

One solution others have proposed to overcome the foregoing shortcomings is to utilize an oversized syringe with a large enough volume to contain the requisite amount of fluid anticipated for administering multiple dosages of anesthetic to the patient over the duration of the procedure. However, such a large syringe may not facilitate convenient operation thereof by the clinician and the bulkiness of the oversize syringe detracts from the maneuverability thereof, thereby often rendering it awkward for the clinician to execute the task of properly infusing anesthetic to the patient. Therefore, it is desirable to provide an I.V. syringe which is relatively compact but which can be conveniently utilized to administer multiple dosages of anesthetic to the patient.

Furthermore, in order to provide a satisfactory rate of anesthetic infusion, it is necessary that the injection be carried out in a gradual and continuous manner to maintain a match between the fluid pressure generated by the syringe and the internal pressure of the vascular system which dictates the infusion rate of the anesthetic to the patient. It has been found that conventional cylindrical plunger-type syringes do not provide the degree of control that clinicians prefer and are often cumbersome to use. Therefore, it is desirable that the I.V. syringe be incorporated in a comfortable pistol grip-type handle such that the clinician may conveniently, and with some degree of precision, operate the syringe to administer accurate and continuous doses of medicinal fluid or anesthetic.

Many pistol grip type-syringe devices have been developed over the years, and by way of example, one syringe device of this type is disclosed in U.S. Pat. No. 4,382,789. This type of pistol grip syringe is now commonplace, for example, in the dental industry and is configured for use with a disposable pre-filled corpule containing therein a predetermined volume of medicinal fluid. The corpule is received within a barrel mounted on the pistol grip assembly, and once so mounted the clinician can pull a control trigger to administer a predetermined volume of fluid to the patient. Although this type of syringe has found acceptance in the industry, the clinician, due to the relatively small volume of fluid typically provided in the corpule, is required to many times over the duration of lengthy procedures to exchange capsules. As such,, this capsules-type syringe suffers from the same shortcomings described above with regard to a conventional syringe. In addition, as with a conventional syringe, it is necessary for the clinician to tally the number of corpules used so that the cumulative total volume of medicinal fluid administered can be monitored. This added task serves to, from time to time, detract the clinician's attention from the procedure underway and constitutes an unnecessary opportunity for human error in the tallying the dosages administered.

Hence, those skilled in the art have recognized the need for a hand held device for administering medicinal fluid to a patient that provides for automatic replenishment of the dosages of fluid as they are administered. As such, it is not necessary for the clinician to suspend his or her operations to manually refill or exchange the syringe each time a new dosage is to be administered. In addition, it is desirable that such device incorporate a cumulative fluid volume indicator to provide the clinician with a visual indication of the cumulative volume of fluid administered during the entire procedure. Furthermore, such a device should incorporate a disposable syringe that facilitates rapid replacement thereof between medical or dental procedures. Such a device should be easy to operate and reliable in use. The present invention meets these needs and others.

SUMMARY OF THE INVENTION

The invention provides a self refilling I.V. syringe for administering medicinal fluid from a fluid supply to a fluid infusion device or applicator.

Briefly and in general terms, the self refilling syringe includes a syringe body device including a plunger chamber open at its rear end and formed at its front end with a connector port. A plunger received in the chamber from the open end and includes a plunger head on one end and a piston on the other. A hub device is mounted on the front end of the syringe body and is formed with a filler port and an applicator port in communication with the connector port. A filler check valve and applicator check valve are disposed in the respective filler and applicator ports. Upon application of a positive pressure thereto from the chamber, the filler check valve closes and simultaneously, the applicator check valve opens to discharge fluid from the chamber through the application port. Upon application of a partial vacuum from the chamber, the applicator check valve closes and the check filler valve opens to replenish the syringe chamber with new fluid.

In a further aspect of the invention, the self refilling syringe includes a holder and the syringe body device is disposable. The syringe body is configured to be releasably mounted to the holder facilitating convenient removal and replacement thereof with a new sterile syringe body between medical or dental procedures. In particular, the holder is formed with a barrel including top and bottom sides further including a syringe mount formed on the top side of such barrel for releasably receiving the syringe body. The holder is also formed with a rearwardly opening, longitudinally extending driver slot wherein a reciprocable drive rod is received therein and is slidable from a forward applicator position to a rear fill position. The drive rod includes on its rear extremity a coupler for coupling to the heat of the plunger and a bias spring is disposed in the driver slot normally biasing the drive rod to its rearward fill position. A pistol grip is mounted on the underside of the barrel and includes a trigger pivotally mounted thereon coupled at its top end to the drive rod such that, upon rotation of the trigger in one direction, the drive rod is driven forwardly in the slot against the bias of the spring carrying the plunger therewith to apply positive pressure to the fluid in the syringe chamber.

In another aspect of the invention, the holder further includes indicia indicative of the quantity of fluid dispensed from the syringe chamber, and an accumulator is coupled with the drive rod including a marker for positioning relative to the indicia. The accumulator is operative upon each rotation of the trigger in the one direction to move the marker relative to the indicia a distance indicative of the volume displaced by movement of the piston in the chamber. Upon repeated rotations of the trigger in the one direction, the marker moves a cumulative distance relative to the indicia to include the cumulative volumetric displacement in the chamber by the cumulative strokes of the piston in the chamber.

In a more particular aspect of the invention, the accumulator is in the form of a rail having a rack of upwardly facing ratchet teeth and is formed with the marker thereon. A pawl is carried pivotally on the drive rod and includes a ratchet tooth selectively engageable with the ratchet teeth such that when the drive rod is driven forwardly, the rachet tooth carries the rail forwardly therewith and, and as the drive rod is driven rearwardly under the bias of the spring, ratchet rearwardly on the rachet teeth.

Other features and advantages of the invention will become apparent from the following detailed description taken in conjunction with the accompanying drawings, which illustrate by way of example, the features of the invention.

BRIEF DESCRIPTION OF THE DRAWINGS

FIG. 1 is a side view of the self refilling I.V. syringe of the present invention;

FIG. 2 is a top plan view of the I.V. syringe shown in FIG. 1;

FIG. 3 is a vertical longitudinal view of the I.V. syringe shown in FIG. 1;

FIG. 4 is a partial transverse sectional view taken along line 4—4 of FIG. 3;

FIG. 5 is a transverse sectional view taken along line 5—5 of FIG. 3;

FIG. 6 is a partial longitudinal sectional view taken along line 6—6 of FIG. 3; and FIG. 7 is an enlarged detail taken from the circle shown in phantom in FIG. 3.

DETAILED DESCRIPTION OF THE PREFERRED EMBODIMENT

As shown in the drawings for purposes of illustration, the invention is embodied in a self refilling I.V. syringe for administering medicinal fluid to a patient that facilitates automatic replenishment of medicinal fluid into the syringe from a fluid supply.

The self refilling I.V. syringe is conveniently hand held and incorporates a disposable syringe body that may be easily exchanged by the clinician in a matter of seconds facilitating rapid replacement thereof between medical or dental procedures. A fluid volume indicator may also be provided to give the clinician a convenient visual indication of the cumulative volume of fluid administered.

Referring now to the drawings and in accordance with the invention, the self refilling I.V. syringe 10, briefly and in general terms, includes a syringe holder 12, which may include a volume indicator 14, mounting a disposable syringe body 16 including a valved hub 22 for selectively driving pressurized medicinal fluid.

With particular reference to FIGS. 1, 2 and 3, the syringe body 16 includes a syringe tube 18 and a plunger, generally indicated at 20. The plunger is configured for slidable receipt within the syringe tube to free fluid through the hub device 22 mounted from distal end 28 of such syringe tube. The syringe tube is formed with a rearwardly opening plunger chamber 24 (FIG. 3) and is configured at its rear extremity with an annular flange 26 (FIG. 2). The distal end 28 of the syringe tube 18 tapers distally and is formed with an axial connector port 30 leading from the chamber 24 (FIG. 3). It is to be appreciated that the hub device 22 may be adaptable for mounting to a conventional off-the-shelf syringe. Alternatively, the hub device may be integrally formed with the syringe tube 18.

With particular reference to FIG. 3, the plunger 20 is of a conventional configuration having an axial plunger rod 32 that may be cruciform in cross section as shown. The rod is formed at its rear end with a circular head or pusher plate 34. An elastomeric piston 36 carrying annular sealing rings 38 is mounted on the distal end of the plunger rod and is sized for wiping engagement against the interior wall of the chamber 24 (FIG. 2). The plunger is extendable in the chamber toward the hub to an application position and retractable away from the hub to a retracted, rear fill position as shown.

Referring to FIGS. 2 and 5, the top forward end of the barrel 90 includes a syringe mount comprising a pair of laterally spaced apart, upwardly projecting, curved resilient gripping members 96. The gripping members curve upwardly laterally outwardly then inwardly and are configured for complementary engagement with the cylindrical outer periphery of the syringe tube 18 for secure gripping thereabout. Projecting vertically upwardly from an intermediate portion of the syringe barrel 90 is a syringe tube mounting bracket 98 formed with an axial upwardly opening slot 100 (FIG. 2) for receipt of plunger rod 32 and the rear end of the syringe tube. The syringe tube bracket is also formed with a transverse vertical, downwardly opening slot 102 for receiving therein the syringe tube flange 26 to restrain the syringe tube 18 from axial movement relative the holder 12.

Referring to FIG. 7, the hub device 22 is generally in the form of a tubular tee fitting configured with a longitudinal run 40 formed on the proximal end with a refill/applicator bore 46 and on its distal end 44 with a fluid application port 80. The applicator port is formed with an enlarged-in-diameter applicator valve chamber 74 configured on its distal end with an annular shoulder 76 and on its proximal end with a conical applicator valve seat 78. The distal end of the longitudinal run 40 is counterbored at 66 for receipt thereinto of an applicator tube 68. A conically shaped applicator check valve poppet 86 is received in the applicator chamber 74 and is biased against the applicator valve seat 78 by means of an applicator coil spring 84 sandwiched between such applicator poppet and the annular shoulder 76. The hub device 22 is further formed with a laterally projecting stem, generally indicated at 42, including a filler port 58 formed with an enlarged-in-diameter filler chamber 54 configured on one end with an annular shoulder 59 and on its opposite end with a conical filler valve seat 56. Disposed in the chamber is a conical filler check valve poppet 60 biased against such seat by a filler coil spring 62 interposed between the shoulder 59 and such filler poppet. The distal end of the bore is counterbored at 48 for receipt of a filler tube 50.

Referring back to FIGS. 1, 2 and 3, the syringe holder 12 is preferably composed of a high strength, translucent, durable plastic and includes an elongated longitudinally projecting syringe barrel 90 having integrally formed therewith a pistol hand hold grip 92 projecting downwardly and rearwardly from the rear end of the barrel. The pistol grip is contoured to be held between the clinician's palm and fingers in a comfortable manner. As shown in FIG. 3, the barrel 90 of the holder 12 is formed with a longitudinal axial plunger driver slot 112 and an axial accumulator slide bore 134, such driver slot and slide bore being arranged in over-under relationship. The plunger driver slot 112 is closed at its forward end and open at its rearward end to receive therein an elongated drive rod 104 of a plunger driver, generally indicated at 94. The plunger driver is axially movable and is engageable with the plunger 20 of the syringe body 16 to drive the plunger within the syringe tube 18 from the retracted fill position to the administration position. As shown in FIG. 3, an elongated retractor spring 114 is received in the driver slot 112 and is interposed between the forward end of the drive rod 104 and the forward closed end of the slot 112 to bias the plunger driver 94 in the rearward direction to drive the plunger to its retracted fill position. The accumulator slide bore 134 has a rectangular cross section (FIG. 5) extending the length of the barrel 90 and is; formed with an open rear end terminating at a closed forward end. The slide bore 134 is configured for slidable receipt therein of an elongated accumulator rail 136 of the volume indicator 14, described in more detail below.

As shown in FIG. 4, the drive rod 104 of the plunger driver 94 is formed at its rear end with a pair of laterally spaced apart, upwardly projecting plunger brackets 106 defining therebetween an axial upwardly opening plunger slot 108 sized to receive therebetween the plunger head 34 of the plunger rod 32. As shown in FIG. 1, the plunger brackets are formed with respective vertical, upwardly opening transverse slots 110 for receiving respectively therein the diametrical opposite ends of the plunger head 34 for coupling the plunger 20 to the plunger driver 94.

The lateral opposite sides of the barrel 90 of the holder 12, adjacent the plunger driver slot 112, are formed with respective longitudinal guide slots 116 (FIG. 1). The distal end of the drive rod 104 of the plunger driver 94 is formed with a transverse bore for press fit receipt therein of a transverse guide pin 118 of a length selected to traverse the drive rod such that the opposite ends thereof project laterally outwardly therefrom to be received in such respective guide slots 116 (FIG. 6). The opposite ends of the guide pin are configured to slide longitudinally in the respective guide slots as the drive rod moves in the driver slot 112. A transverse driver pin 132 is mounted at the rear end of the plunger drive rod 104 below the plunger brackets 106 to couple an elongated trigger lever, generally indicated at 120, to the plunger driver 94.

The trigger lever 120 is pivotally mounted from the upper front side of the pistol grip 92. The trigger lever is pivoted at an intermediate trigger pivot 122 to the pistol grip 92 angling outwardly and downwardly therefrom. The portion of the trigger lever below the pivot point defines a finger grip 124. As shown in FIG. 4, the top end of the trigger lever is forked and spaced apart to flank the opposite sides of the pistol grip 92. The respective top ends of the forked trigger lever are coupled to forward link pivots 128 of a pair of respective trigger links 130 (FIG. 1) disposed on the opposite sides of the pistol grip. As shown in FIGS. 4 and 6, the respective rear ends of the trigger links 130 are pivoted from the lateral opposite ends of the transverse driver pin 132 at the rear end of the plunger drive rod 104.

With particular reference to FIG. 3, the cumulative volume indicator 14 will be described hereinafter in detail. The volume indicator 14 is shown for illustrative purposes as a linear indicator comprising the accumulator rail 136 that provides the clinician with a visual indication of the cumulative total volume of fluid dispensed from the syringe chamber 24. It will be recognized by those skilled in the art that the cumulative indicator may take many different mechanical, hydraulic or electrical forms. As an example, a gear driven dial indicator could be operatively connected to a linear gear disposed on the plunger driver 94 to provide a cumulative indication of fluid administered. Likewise, a fluid dial could be provided with a transparent strip into which indicator fluid is pumped and accumulated during each procedure.

In the preferred embodiment, the forward tip of the accumulator rail 136 is formed with an indicator marker 138 that may simply be a colored vertical stripe. Disposed adjacent the length of the accumulator bore 134 on the outside surface of the holder barrel 90 are volume indicia 145 spaced equidistantly apart along the length of such barrel. Because the holder is preferably composed of a relatively clear translucent material, the clinician can see through the holder barrel 90 to visualize the colored marker relative to the scaled indicia so that a volume indication of fluid dispensed is provided. Alternatively, a sight channel could be formed longitudinally adjacent the accumulator slide bore 134 that would allow the clinician to visualize the marker through such sight channel.

The rear end of the accumulator rail 136 is formed with an increased-in-diameter circular reset grip 140 for convenient grasping by the clinician for resetting the indicator 14 as described below. The top end of the accumulator rail is formed along its length with a rack of closely spaced apart rearwardly and upwardly ramped saw teeth 142 configured for racheting engagement with an L-shaped pawl 144 mounted at the rear end of the plunger driver 94 adjacent to and above the accumulator slide bore 134.

The pawl 144 is freely pivoted from the transverse driver pin 132 and is formed with a downwardly projecting pointed engagement tooth 142 for engaging the rear end of the respective teeth 142 to block rearward retraction of the accumulator rail 136 relative the holder 12 (FIG. 3). A torsional pawl spring (root shown) applies a clockwise rotational force to the pawl, as viewed in FIG. 3, to bias the engagement tooth into engagement with the saw teeth 142 of the accumulator rail 136. The pawl is also formed with rearwardly projecting thumb release lever 148, whereupon downward depression thereof pivots the pawl against the bias of the torsional spring to free the engagement tip from the rachet saw teeth so that the accumulator rail may be reset.

With reference to FIGS. 1 and 2, the technique for mounting the syringe body 16 to the syringe mount of the holder 12 will be described. When the clinician is preparing for the infusion procedure, the clinician may retrieve a sterile disposable syringe body 16 from a sterile package and pull the plunger 20 thereof to its retracted position. The clinician may then grasp the holder in one hand and the syringe body in the other hand to overlie such syringe body over such holder. The clinician may then align the syringe tube flange 26 with the upwardly opening slot 102 of the syringe tube bracket 98 and align the plunger flange 34 of the plunger 20 with the plunger slot 110 of the plunger brackets 106. He or she may then guide the syringe body 16 downwardly relative the holder such that the syringe tube 18 contacts the upper extremities of the resilient gripping members 96 of the syringe mount. The syringe tube is then forcibly pressed downwardly, spreading the upper ends of the gripping members 96 laterally such that the syringe tube 18 is passed between such upper ends to allow such resilient gripping members to return to their predetermined shape positively gripping the outer periphery of the syringe tube therebetween (FIG. 5). Simultaneously, the respective flanges 26 and 34 are received in the respective slots 102 and 110 of the syringe bracket 98 and the plunger brackets 106. It is to be appreciated that the syringe body 16 may be mounted to the holder 12 in a matter of seconds. To prepare the self-refilling I.V. syringe 10 for use, the free end of the fluid filler tube 50 may then be connected to a fluid supply such as an inverted bottle, and the free end of the applicator tube 68 connected to, for instance, an infusion cannula.

Referring now to FIGS. 1 and 3, with the syringe body 16 properly mounted to the holder 12 and the plunger 20 at its retracted position within the syringe tube 18 as shown, the syringe chamber 24 of the syringe body 16 is in position to be filled with I.V. fluid or anesthetic. To initially fill the syringe chamber 24, the clinician can conveniently grasp the pistol grip 92 of the holder 12 in the palm of his hand and place his or her fingers on the finger grip 126 of the trigger lever 120 and depress such trigger lever 120. The clinician may then depress the trigger lever to rotate such lever in one direction (clockwise in the view shown in FIG. 1) to pivot about the trigger pivot 122. The upper end of the trigger lever follows an arcuate path carrying the respective trigger links 130 therewith in a forward direction. The trigger links translate the arcuate motion of the trigger lever to a linear motion carrying the plunger driver 94 therewith in a linearly forward direction. The plunger driver 94 then drives the plunger 20 engaged therewith and the piston 36 thereof distally in the syringe chamber 24 toward the hub 28 to simultaneously contract the retractor spring 114 and pressurize the air in the chamber 24. With reference to FIG. 7, the air pressure applies a closing force against bottom surface of the filler valve poppet 60 in the filler chamber 54 to cooperate with the filler coil spring 62 in applying a positive seal between the filler poppet 60 and the filler seat 56 closing off fluid flow through the filler port 58. The air pressure is also applied to the proximal end of the applicator valve poppet 86 to drive such poppet distally against the bias of the applicator coil spring 84 to lift such poppet 86 off its applicator valve seat 78 to open the applicator port 80. As such, air passes through the applicator port 80 around the periphery of the applicator poppet, through the applicator chamber 74 to exhaust air through the applicator tube 68.

When the trigger lever 120 is released, the retractor spring 114 biases the plunger driver 94 rearwardly to carry the plunger 20 therewith to its retracted position shown. As such, the plunger piston 36 draws a partial vacuum within the syringe chamber 24. With reference to FIG. 7, the partial vacuum is applied to the proximal side of the applicator valve poppet 86 allowing the force of the applicator coil spring 84 coupled with atmospheric pressure, to close such poppet on the applicator valve seat 78. Simultaneously, such partial vacuum from the chamber 24 will be imparted through the refill/applicator bore 46 and filler port 78 to the bottom side of the filler poppet 60 causing the atmospheric pressure on the fluid upstream of such poppet to overcome the bias of the filler spring 62 to contract such spring moving such filler poppet out of engagement with the filler seat 56. As such, fluid is drawn from the supply reservoir through the fluid filler tube 50 around the periphery of the filler poppet 60, into the filler chamber 54, to the filler port 58 and through the refill/applicator bore 46 filling the syringe chamber 24 with fluid. The trigger may be actuated or pumped a number of times until all air is completely evacuated from such chamber and fluid applicator tube 68. The self refilling I.V. syringe 10 is now ready for use in administering fluid to the patient.

With the syringe chamber 24 operatively filled with I.V. fluid in a manner described above, the trigger lever 120 may be operated in the same manner as described above to dispense such I.V. fluid to the patient. As the trigger lever is depressed, the plunger driver 94 drives the piston 36 of the plunger 20 distally in the syringe chamber 24 to pressurize the fluid in the chamber 24. Similarly as described above, the fluid pressure applies a closing force against bottom surface of the filler poppet 60 in the filler chamber 54 to drive such filler poppet 60 against the filler seat 56 to positively close off fluid flow through the filler port 58. Simultaneously, the pressure applied to the proximal end of the applicator poppet 86 drives such poppet distally against the bias of the applicator spring 84 to lift such poppet off its seat 78 to open the applicator port 80. As such, fluid passes through the applicator port 80 around the periphery of the applicator poppet 86, through the applicator chamber 74 to dispense fluid through the applicator tube 68 to the patient.

The clinician may depress the trigger lever 120 at a controlled rate for an entire stroke to drive the piston 36 of the plunger 20 the length of the syringe chamber 24 to fully deplete the fluid contained therein dispensing the entire volume of the chamber to displace a like amount to the patient. Alternatively, the clinician may depress the trigger lever only partially to deplete only a portion of the volume contained in the chamber as desired.

Simultaneously as the trigger lever 120 is being depressed, such trigger lever carries the pawl 144 of the volume indicator 14 in engagement with an adjacent saw tooth 142 of the accumulator rail 136 to drive such rail forwardly in the accumulator bore 134 of the holder 12. As such, the indicator marker 138 (FIG. 3) on the rail 136 is moved forwardly relative to the indicia 145 on the holder to provide an indication of the fluid administered to the patient.

When the trigger lever 120 is released, the retractor spring 114 biases the plunger driver 94 rearwardly to carry the plunger 20 therewith to its retracted position. Retraction of the plunger piston 36 serves to draw a partial vacuum within the syringe chamber 24 and on the proximal side of the applicator poppet 86 allowing the force of the applicator coil spring 84, coupled with atmospheric pressure, to close such poppet on the applicator valve seat 78. Simultaneously, such partial vacuum is communicated to the bottom side of the filler poppet 60 to cause the atmospheric pressure on the fluid upstream of such poppet to overcome the bias of the filler spring 62 to move such filler poppet out of engagement with the filler seat 56 to draw fluid from the supply reservoir through the fluid filler tube 50, filler port 58 and refill/ applicator bore 46 to replenish the syringe chamber 24 with a new volume of fluid.

Simultaneously as the trigger lever 120 is released, the trigger carries the pawl 144 of the indicator 14 rearwardly to slide the engagement tooth 146 thereof over the ramped portions of the rachet teeth 142 of the accumulator rail 136. When the plunger driver 94 is in its retracted position, the engagement tooth 146 of the pawl 144 will pivot in the clockwise direction, in the view shown in FIG. 3, to engage an adjacent saw tooth 142 of the accumulator rail 136, such that the engagement tooth is positioned to drive such rail forward with the next trigger stroke.

As the clinician depresses the trigger lever a second time to dispense a second volume of fluid to the patient, the pawl 144 is in position to again drive the accumulator rail 136 further forward in the accumulator bore 134 moving the indicator marker 138 further forward relative to its first position and relative to the indicia 145 on the barrel 90 of the holder 12. Because the length of the accumulator bore 134 is much longer than the length of a single stroke of the plunger 20, the accumulator rail 136 may be reengaged and driven progressively a multitude of times to provide a cumulative indication of fluid dispensed.

To reset the fluid volume indicator 14, the release lever 148 of the pawl 144 may be depressed downwardly to pivot such pawl about the transverse driver pin 132 and lift the engagement tooth 146 thereof upwardly free of the rachet teeth 142 of the accumulator rail 136. With the release lever depressed, the clinician may grasp the reset grip 140 at the rear end of the accumulator rail and pull such rail rearwardly within the accumulator bore 134 to move the marker 138 rearward to a zeroed indication relative the indicia 145 (not shown). The release lever may then be released to allow the pawl to pivot clockwise, as viewed in FIG. 3, to drive the tooth 146 downwardly under the biasing force of the torsional spring to engage an adjacent saw tooth 142. The indicator is now reset for the next infusion procedure.

Once the infusion procedure has been concluded, removal of a used syringe body 16 may be made by simply grasping the syringe body and pulling upwardly on the assembly relative to the holder 12. As such, the syringe tube 18 will be released from the gripping members 96 and the respective plunger and syringe tube flanges 34 and 26 will be withdrawn from the respective plunger bracket and syringe tube bracket slots 110 and 102. Thereafter, a new syringe body may be retrieved and mounted to the holder for the next infusion procedure.

From the foregoing it can be appreciated that the self-refilling I.V. syringe provides a compact, comfortable hand held device for conveniently administering medicinal fluid to a patient and includes a means for facilitating automatic replenishment of a volume of fluid previously administered. As such, the clinician is not required to suspend his or her operations and detract his or her attention away from the matter at hand to periodically refill the syringe manually. The syringe incorporates a fluid volume indicator to provide the clinician with a convenient visual indication of the cumulative volume of fluid administered. In addition, the syringe is disposable and facilitates rapid replacement thereof between I.V. infusion procedures. The self-refilling syringe is easy to operate and reliable in use.

While particular forms of the invention have been illustrated and described, it will be apparent that various modifications can be made without departing from the spirit and scope of the invention.

What is claimed is:

1. A tallying self-filling syringe apparatus comprising:

a holder;

a self-filling syringe mounted on said holder, including a reciprocal plunger, said plunger being retractable to draw fluid medicinal fluid thereinto from a bulk supply and advanceable to drive said medicinal fluid out an outlet;

a driver moveably mounted on said holder, said driver being advanceable to advance said plunger and retractable to retract said plunger;

an indicator formed on said holder and including indicia indicative of the cumulative quantity of said medicinal fluid driven out said outlet; and an accumulator coupled with said drive and including an active and passive mode, said accumulator being operative in said active mode upon said plunger being advanced to register with the indicia indicative of the quantity of said medicinal fluid driven out said outlet and being passive during retraction of said plunger to leave said indicia indicative of the quantity of medicinal fluid previously driven out said outlet and then during the subsequent advancement of said plunger being operative in said active mode to register the indicia indicative of the cummulative medicinal fluid driven out said outlet.

2. A self-refilling syringe apparatus as set forth in claim 1 that includes:

a trigger movably mounted on said holder and coupled with said driver to, upon movement of said trigger from a first position to a second position, advance said driver.

3. A self-refilling syringe apparatus as set forth in claim 1 wherein:

said holder includes a slide; and said accumulator includes a rail co-extensive with said plunger and moveably received in said slide and a coupler responsive to advancement of said driver to actively advance said rail and to retraction of said driver to passively disengage said rail.

4. A self-refilling medicinal syringe apparatus comprising:

a syringe including a syringe barrel having a plunger therein projecting from one end thereof to terminate in a head and including on its end opposite said one end a hub including one way inlet and outlet valves responsive, respectively, to a predetermined partial vacuum and a selected pressure in said barrel to open and close respectively and for connection, respectively, to a supply of medicinal fluid and to an intravenous applicator;

a holder including a hand hold grip and a trigger movably carried from said holder for reciprocating back and forth through a trigger path between a first and a second position;

an indicator formed on said holder and including indicia indicative of the cumulative quantity of medicinal fluid administered from said outlet valve;

a spring bias to drive said trigger to said first position;

a receiver on said holder for removably receiving and holding said syringe barrel;

a driver movably carried on said holder for travel therealong and including a bracket for engaging said head to carry said plunger therewith for movement of said plunger relative to said barrel;

a linkage linking said trigger to said driver and operable in response to said trigger being reciprocated between said first to said second positions for advancing and retracting said driver to advance and retract said plunger in said barrel whereby said syringe may be mounted in said receiver, said bracket of said driver engaged with said head, and said inlet valve connected with said supply of medicinal fluid and said trigger released for said spring to move it to said first position to retract said plunger in said barrel to draw said predetermined partial vacuum to close said outlet valve to cause said partial vacuum to be created in said barrel to draw said medicinal fluid into said barrel so that when said trigger is moved from said first to said second position causing said plunger to be advanced to generate a positive pressure on said medicinal fluid in said barrel to drive said medicinal fluid out said outlet valve; and an accumulation sensor coupled to said driver and cooperating with said indicator to operate in response to consecutive advancements of said plunger to total the cumulative advancements and drive said indicator to the indicia corresponding with said cumulative advancements.

5. A self-refilling syringe apparatus as set forth in claim 4 wherein:

said holder is formed with a slide;

said indicia is spaced along said slide and further including:

a rail for sliding in said slide and including a pointer for pointing to said indicia and wherein said apparatus includes:

a ratchet mounted on said driver and removably engagable with said rail to, when said trigger is moved from said first to said second position driving said driver in one direction, engage said rail to draw said rail in one direction to drive said pointer in a forward direction relative to said indicia and operative upon said trigger moving from said second to said first position, disengage said rail and upon said trigger being moved from said first to said second position, to re-engage said rail to thereby cause said rail to progressively carry said pointer forwardly relative to said indicia with each successive stroke of said trigger from said first to said second positions.

* * * * *